United States Patent [19]

Geigert et al.

[11] Patent Number: 4,587,217

[45] Date of Patent: * May 6, 1986

[54] VICINAL HETEROGENEOUS DIHALOGENATED PRODUCTS AND METHOD

[75] Inventors: John Geigert, Clayton; Saul L. Neidleman, Oakland, both of Calif.

[73] Assignee: Cetus Corporation, Emeryville, Calif.

[ * ] Notice: The portion of the term of this patent subsequent to Jan. 17, 2001 has been disclaimed.

[21] Appl. No.: 607,723

[22] Filed: May 7, 1984

Related U.S. Application Data

[63] Continuation-in-part of Ser. No. 364,920, Apr. 2, 1982, abandoned.

[51] Int. Cl.$^4$ .................. C12P 7/34; C12N 9/08; C12N 9/02; C12R 1/645
[52] U.S. Cl. ................... 435/155; 435/192; 435/189; 435/911; 435/41
[58] Field of Search ........ 435/123, 132, 171, 155–156, 435/190, 192, 189, 911

[56] References Cited

U.S. PATENT DOCUMENTS

| | | |
|---|---|---|
| 3,576,893 | 4/1971 | Baird, Jr. . |
| 4,147,733 | 4/1979 | Fiske et al. . |
| 4,247,641 | 1/1981 | Neidleman et al. . |
| 4,282,324 | 8/1981 | Neidleman et al. ................ 435/171 |
| 4,284,723 | 8/1981 | Neidleman et al. ................ 435/123 |
| 4,426,449 | 1/1984 | Geigert et al. ..................... 435/155 |

FOREIGN PATENT DOCUMENTS 2028173  3/1980  United Kingdom .

OTHER PUBLICATIONS

Hallenberg et al, "Purification of Chloroperoxidase from *Caldariomyces fumago*", Methods in Enzymology, 52, pp. 521–529 (1978).
Riemschneider, Chem. Abs., 55, 63, 6360e.
de la Mare et al, J. Chem. Soc. (1962) pp. 443–449.
Cornforth et al, J. Chem. Soc. (C) (1970) pp. 846–849.
M. A. Pickard, Can. J. Microbiol., 27, 1298–1305 (1981).
T. D. Lee et al., Biochem. Biophys. Res. Comm., 110, 880–883 (1983).
S. L. Neidleman and J. Geigert, Trends in Biotech., 1, 21–25 (1983).
S. L. Neidleman et al., "Enzymatic Halogenation of Allyl Alcohol to 2,3-Bromochloro-, Bromoiodo-, and Fluoroiodo-1-Propanols: A Study at the Interface of Chemical and Enzymatic Catalyses", in *Enzyme Technology*, III. Rothenburg Fermentation Symposium 1982, Ed. by R. M. Lafferty, Springer–Verlag, New York, 1983, pp. 79–90.
Johnson, R. L. et al, *Journal of Physical Chemistry*, vol. 71, 1967, pp. 4366–4383.
Roth, Herbert et al, *Journal of Economic Entomology*, vol. 63, 1970, pp. 496–499.
Rylander, Paul, *Catalytic Hydrogenation in Organic Synthesis*, Ch. 13, 1979, pp. 235–250.
Morrison, Martin et al, *Annual Reviews of Biochemistry*, vol. 45, 1976, pp. 861–888.
Hager, Lowell P. et al, *Journal of Biological Chemistry*, vol. 241, 1966, pp. 1769–1777.
Bakkenist, A. R. J., et al, *Biochimica et Biophysica Acta.*, vol. 613, 1980, pp. 337–348.
Morris, David R. et al, *Journal of Biological Chemistry*, vol. 241, 1966, pp. 1763–1768.
Cooney, Charles L. et al, *Biotechnology and Bioengineering*, vol. 16, 1974, pp. 1045–1053.

*Primary Examiner*—Thomas G. Wiseman
*Assistant Examiner*—John Tarcza
*Attorney, Agent, or Firm*—Albert P. Halluin; Elliott L. Fineman

[57] ABSTRACT

A method is provided for the production of vicinal heterogeneous dihalogenated products from alkenes and alkynes. The alkene or alkyne is reacted in an aqueous solution of salts of two different halides, an oxidizing agent and an halogenating enzyme. Products provided by the method include novel 2,3-heterogeneously dihalogenated-1,4-butanediols.

19 Claims, No Drawings

VICINAL HETEROGENEOUS DIHALOGENATED PRODUCTS AND METHOD

This is a continuation-in-part of application Ser. No. 364,920, filed Apr. 2, 1982, abandoned.

This invention relates generally to an enzymatic process for making useful commercial products from alkenes and alkynes and novel products of such a process. More particularly, the invention relates to an improved process for the production of vicinal, heterogeneous dihalogenated products from alkenes and alkynes wherein an enzyme is used to effect the reaction. Also more particularly, the invention relates to an improved process for the production of fluorinated products from alkenes and alkynes wherein an enzyme is used to effect the reaction.

Vicinal, heterogeneous dihalogenated products are useful as solvents, chemical intermediates, refrigerants, fumigants, and in many other ways. Vicinal chloroiodo compounds (I) and vicinal bromochloro compounds (II) have found application in the agricultural chemical field as soil fumigants and pesticidal agents (U.S. Pat. No. 3,576,893, Baird Jr. et al, 1971; Roth et al, *J. Economic Entomology* 63, 496 (1970)). In addition, the vicinal bromochloro group (II) imparts flame retarding capability into plastics and fibers (Pol. Patent No. 105,589, Dul et al, 1980). 1,2-Chlorofluorethane (III) is useful both as a refrigerant and as a solvent for recovering coal from mixtures (U.S. Pat. No. 4,147,733, Fiske et al, 1979; U.K. Pat. application No. 2,028,173 A. Keller et al, filed Aug. 3, 1979).

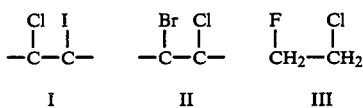

Owing to differences in chemical reactivity of the different carbon-halogen bonds, one halogen atom may be selectively removed either chemically or enzymatically from these vicinal, heterogeneous dihalogenated products. Thermal decomposition or photolysis of 1,2-bromochloroethane (IV) preferentially yields vinyl chloride (V) over vinyl bromide (VI) (Johnson et al, *J. Physical Chemistry* 71, 4366 (1967)):

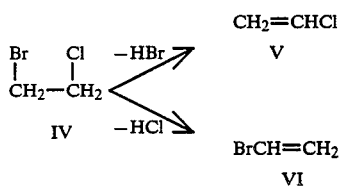

Catalytic hydrogenation preferantially dehydrohalogenates in the following order: I>Br>Cl>F; thus, permitting the production of fluorine-containing products from the vicinal, heterogeneous dihalogenated products (Rylander, *Catalytic Hydrogenation in Organic Synthesis*, 235 (1979)):

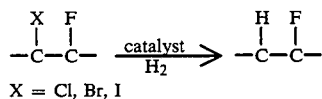

Fluorine imparts biological effects useful in drugs and other bioactive compounds.

Known processes for producing the vicinal dihalogenated products from alkenes and alkynes typically involve the addition of alkene or alkyne and free heterogeneous halogen in a reactor under controlled conditions. The use of free heterogeneous halogen in these processes requires expensive control procedures and equipment to prevent loss of this toxic and corrosive reactant. Also, the use of free heterogeneous halogen is now preferably avoided because of the energy-intensive process employed for its production.

An improved process is provided by the present invention for producing vicinal, heterogeneous dihalogenated products from alkenes and alkynes. The enzymatic halogenating process of the present invention has several advantages over the present state of the art for producing vicinal, heterogeneous dihalogenated products from alkenes and alkynes, including the following: The use of inexpensive, less dangerous, inorganic halides, rather than elemental halogen or expensive reagents, i.e., chloride ion plus bromide ion rather than bromine chloride, fluoride ion plus iodide ion rather than iodine fluoride or antimony trifluoride and iodine; the use of ambient temperature; and the use of standard or close to standard atmospheric pressure.

In addition to proceeding favorably at room temperature, this enzymatic process involves the use of dilute $H_2O_2$, not necessarily purified. The $H_2O_2$ may be added directly or generated in situ by an enzymatic or chemical reaction. This reduces the cost of the $H_2O_2$ as compared to the cost of concentrated, purified material; increases the safe useage of the substance; and extends the life of the halogenating enzyme.

Accordingly, it is an object of the present invention to provide a process for preparing vicinal heterogeneous dihalogenated products from alkenes and alkynes.

It is also an object of the present invention to prepare these compounds without using free halogen.

It is a further object of the present invention to provide a low cost process for producing the desired products from alkenes and alkynes.

Very generally, the method of the invention produces vicinal, heterogeneous dihalogenated products from alkenes and alkynes by providing in a reaction vessel a mixture of halogenating enzyme, an oxidizing agent and two different halide ions. An alkene or alkyne is then introduced into the vessel and maintained in contact with the reaction mixture for a sufficient period of time to convert the alkene or alkyne to the desired vicinal, heterogeneous dihalogenated product.

The present invention is based on the discovery that the group of enzymes classified as haloperoxidases acts upon alkenes and alkynes to produce vicinal, heterogeneous dihalogenated products. These products are characterized by the structural formula:

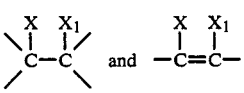

where X and $X_1$ are selected from a group consisting of either fluoride, chloride, bromide or iodide, but where $X \neq X_1$.

Prior art processes teach that haloperoxidase produces vicinal, homogeneous dihalogenated products from alkenes and alkynes (Geigert and Neidleman, U.S. Pat. No. 4,426,447).

Alkene

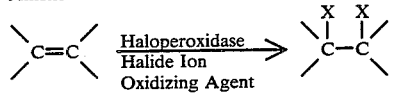

Alkyne

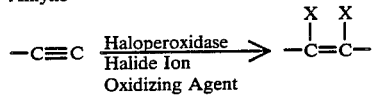

However, prior art processes do not teach that vicinal, heterogeneous dihalogenated products can be produced from alkenes and alkynes by haloperoxidase:

Alkene

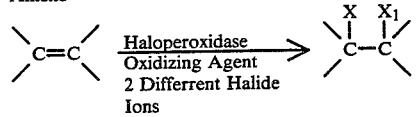

Alkyne

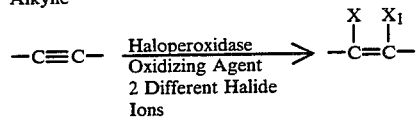

(where $X \neq X_1$)

Moreover, from these prior art processes it was not obvious to run the alkene and alkyne reactions in the presence of two different halide ions. Morrison et al (Ann, Rev. Biochem. 45, 861 (1976)) state that chloroperoxidase is the only one of the haloperoxidases studied that is known to be influenced by the presence of halide ion mixtures. Both chloride and bromide in concentrations up to 0.1M greatly enhanced iodination of thyroglobulin. Although this stimulation was observed, only homogeneous monohalogenated product was observed. Hager et al (J. Biol. Chem. 241, 1769 (1966)) state that fluoride ion when present with chloride ion inhibits the chlorination of monochlorodimedon by chloroperoxidase. Bakkenist et al (Biochim. Biophys. Acta 613, 337 (1980)) reported the same effect of fluoride ion on the bromination of monochlorodimedon by myeloperoxidase. But in none of these reports was there any evidence presented for heterogeneous dihalogen addition. Therefore, it was not obvious that haloperoxidase would produce vicinal, heterogeneous dihalogenated products from alkenes and alkynes when the enzymatic reactions were run in the presence of two different halide ions.

In accordance with this invention, a process has been developed for the production of vicinal, heterogeneous dihalogenated products.

Prior art teaches that haloperoxidases can incorporate only certain halides (Morrison et al, Ann. Rev. Biochem. 45, 861 (1976)):

| Haloperoxidase | Halides that can be incorporated | Halides that cannot be incorporated |
|---|---|---|
| myeloperoxidase | Cl$^-$, Br$^-$, I$^-$ | F$^-$ |
| chloroperoxidase | Cl$^-$, Br$^-$, I$^-$ | F$^-$ |
| lactoperoxidase | Br$^-$, I$^-$ | F$^-$, Cl$^-$ |

-continued

| Haloperoxidase | Halides that can be incorporated | Halides that cannot be incorporated |
|---|---|---|
| bromoperoxidase | Br$^-$, I$^-$ | F$^-$, Cl$^-$ |
| thyroid peroxidase | I$^-$ | F$^-$, Cl$^-$, Br$^-$ |
| horseradish peroxidase | I$^-$ | F$^-$, Cl$^-$, Br$^-$ |

In accordance with this invention, a process has been developed for the production of vicinal, heterogeneous dihalogenated products that contain halogen atoms not previously demonstrated to be incorporated by haloperoxidases.

It is also an object of the present invention to provide 2-bromo-3-iodo-1-propanol; 3-bromo-2-iodo-1-propanol; 3-fluoro-2-iodo-1-propanol; 2-fluoro-3-iodo-1-propanol; 2-fluoro-3-chloro-1,4-butanediol; 2-fluoro-3-bromo-1,4-butanediol; 2-fluoro-3-iodo-1,4-butanediol; 2-chloro-3-iodo-1,4-butanediol; 2-bromo-3-iodo-1,4-butanediol and 2-bromo-3-chloro-1,4-butanediol as respective new compositions of matter.

Other objects of the present invention will become more apparent from the following detailed description and accompanying claims.

The alkenes useful in the process of the invention can be broadly defined as any hydrocarbon containing a carbon-to-carbon double bond, represented by the following structural formula:

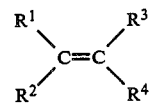

wherein each of $R^1$, $R^2$, $R^3$ and $R^4$ is selected from a group consisting of:

| (1) hydrogen | |
|---|---|
| (2) a straight chain | saturated or unsaturated |
| (3) a branched chain | hydrocarbon radical |
| (4) a cyclic | |

Representative alkenes are:

| Alkene | $R^1$ | $R^2$ | $R^3$ | $R^4$ |
|---|---|---|---|---|
| ethylene | H | H | H | H |
| propylene | CH$_3$ | H | H | H |
| butene-1 | C$_2$H$_5$ | H | H | H |
| pentene-1 | C$_3$H$_7$ | H | H | H |
| octene-1 | C$_6$H$_{13}$ | H | H | H |
| decene-1 | C$_8$H$_{17}$ | H | H | H |
| dodecene-1 | C$_{10}$H$_{21}$ | H | H | H |
| isobutylene | CH$_3$ | CH$_3$ | H | H |
| cis-butene-2 | CH$_3$ | H | CH$_3$ | H |
| trans-butene-2 | CH$_3$ | H | H | CH$_3$ |
| 2-methyl-butene-2 | CH$_3$ | CH$_3$ | CH$_3$ | H |
| 1,3-butadiene | CH$_2$=CH | H | H | H |
| 1,4-pentadiene | H$_2$C=CHCH$_2$ | H | H | H |
| isoprene | H$_2$C=C(CH$_3$) | H | H | H |
| 1,7-octadiene | H$_2$C=CH(CH$_2$)$_4$ | H | H | H |

The broad definition of alkenes includes alkenes where $R^1$, $R^2$, $R^3$, and/or $R^4$ can be an aromatic or heteroatom-containing group, provided that the substituents are inert to the prescribed reaction conditions, or do not deactivate the normally reactive carbon-to-carbon double bond.

Representative alkenes containing such aromatic or heteroatom groups are:

| Alkene | R$^1$ | R$^2$ | R$^3$ | R$^4$ |
|---|---|---|---|---|
| allyl chloride | ClCH$_2$ | H | H | H |
| allyl bromide | BrCH$_2$ | H | H | H |
| allyl alcohol | HOCH$_2$ | H | H | H |
| 2-butene-1,4-diol | HOCH$_2$ | H | HOCH$_2$ | H |
| 2-buten-1-ol | HOCH$_2$ | H | H | CH$_3$ |
| 3-buten-1-ol | HO(CH$_2$)$_2$ | H | H | H |
| 4-penten-1-ol | HO(CH$_2$)$_3$ | H | H | H |

The R groups can also be connected to form a cyclic ring. A representative cyclic alkene is 2-cyclohexen-1-ol (VII).

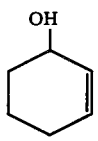

OH    VII

The alkynes useful in the process of the invention can be broadly defined as any hydrocarbon containing a carbon-to-carbon triple bond, represented by the following structural formula:

$$R^1-C\equiv C-R^2$$

wherein each of R$^1$ and R$^2$ is selected from a group consisting of:

| (1) hydrogen | |
|---|---|
| (2) a straight chain | saturated or unsaturated |
| (3) a branched chain | hydrocarbon radical |
| (4) a cyclic | |

Representative alkynes are:

| Alkyne | R$^1$ | R$^2$ |
|---|---|---|
| methyl acetylene | CH$_3$ | H |
| ethyl acetylene | CH$_3$CH$_2$ | H |
| 1-phenyl-1-propyne | C$_6$H$_5$ | CH$_3$ |
| propargyl alcohol | HOCH$_2$ | H |
| 2-butyne-1,4-diol | HOCH$_2$ | HOCH$_2$ |
| 3-butyn-1-ol | HO(CH$_2$)$_2$ | H |

The present invention makes use of haloperoxidase enzymes. Such enzymes include chloroperoxidase derived from the microorganism *Caldariomyces fumago*, bromoperoxidase derived from algae, lactoperoxidase derived from milk, thyroid peroxidase derived from thyroid, myeloperoxidase derived from leukocytes, and horseradish peroxidase derived from horseradish. Certain of these haloperoxidases are commercially available.

The preferred haloperoxidase depends upon the products desired. The halides that the given haloperoxidases can use are listed below:

| Haloperoxidase | Halides, X$^-$ | Halides, X$_1^-$ |
|---|---|---|
| myeloperoxidase | Cl$^-$, Br$^-$, I$^-$ | F$^-$, Cl$^-$, Br$^-$ |
| chloroperoxidase | Cl$^-$, Br$^-$, I$^-$ | F$^-$, Cl$^-$, Br$^-$ |
| lactoperoxidase | Br$^-$, I$^-$ | F$^-$, Cl$^-$, Br$^-$ |
| bromoperoxidase | Br$^-$, I$^-$ | F$^-$, Cl$^-$, Br$^-$ |
| thyroid peroxidase | I$^-$ | F$^-$, Cl$^-$, Br$^-$ |
| horseradish peroxidase | I$^-$ | F$^-$, Cl$^-$, Br$^-$ |

| Haloperoxidase | Halides, X$^-$ | Halides, X$_1^-$ |
|---|---|---|
| (where X$^- \neq$ X$_1^-$) | | |

If it is desired to halogenate with iodide and bromide, the preferred halogenating enzyme will be an iodoperoxidase (horseradish peroxidase or thyroid peroxidase). If it is desired to halogenate with iodide and chloride, the preferred halogenating enzyme will be an iodoperoxidase or a bromoperoxidase (bromoperoxidase or lactoperoxidase). It it is desired to halogenate with iodide and fluoride, an iodoperoxidase, bromoperoxidase or chloroperoxidase may preferably be employed. Where it is desired to halogenate with bromide and fluoride, preferred halogenating enzymes are bromoperoxidases or chloroperoxidases (myeloperoxidase, or chloroperoxidase from *C. fumago*). Where the halogenation is to be by bromide and chloride, the preferred halogenating enzyme is a bromoperoxidase. Finally, when the halogenation is to involve chloride and fluoride, the preferred halogenating enzyme is chloroperoxidase.

For ease of discussion, various aspects of the present invention are described below particularly, but not exclusively, in connection with the use of the preferred peroxidase, chloroperoxidase, derived from *Caldariomyces fumago* (obtained from the American Type Culture Collection, Rockville, Md. (ATCC) under Deposit No. 16373). Cultures of *C. fumago* (ATCC 16373) have been grown and deposited by the assignee of the present application with the Northern Regional Research Laboratory, Peoria, Ill. (NRRL) under NRRL Deposit No. 15272. This deposit with the NRRL was made under the terms of the Budapest Treaty on the International Recognition of the Deposit of Microorganisms for the Purposes of Patent Procedure and Regulations promulgated thereunder. The microorganism, *Caldariomyces fumago*, may be grown as a static or agitated, submerged culture in Czapek-Dox medium at room temperature for 3 to 10 days by conventional methods. The halogenating enzyme, chloroperoxidase, is prepared from an aqueous homogenate of the mycelial pads of the microorganism grown under static conditions or from the filtrate of the microorganism grown under static or agitated submerged culture conditions. Detailed descriptions for preparing chloroperoxidase can be found in the following articles and patent: (1) U.S. Pat. No. 4,247,641, Neidleman et al, 1981; (2) Morris et al, *J. Biol, Chem.* 241, 1763, (1966); and (3) Cooney et al, *Biotech, Bioeng.* 16, 1045, (1974); Pickard, *Can. J. Microbiol.* 27, 1298–1305 (1981). *C. fumago* chloroperoxidase can also be purchased in crude and, preferably, purified forms from Sigma Chemical Company, St. Louis, Mo.

The halogenating enzyme may also be used in an immobilized form. Processes for enzyme immobilization are familiar to those skilled in the art, and include reacting either a solution of the enzyme or a suspension of enzyme containing cells with one of a broad range of organic or inorganic supports. Included among these are polyacrylamide, ethylene-maleic acid copolymers, methacrylic-based polymers, polypeptides, styrene-based polymers, agarose, cellulose, dextran, porous glass beads, and aluminum or titanium hydroxide. Enzymes in this form have increased stability, extended life and usefulness, and recoverability. Reactions employing immobilized enzymes may be run in columns or reaction tanks.

In addition to the halogenating enzymes, an oxidizing agent is required in the reaction mixture. A preferred oxidizing agent is hydrogen peroxide, which may be added directly to the mixture in a single batch addition, or in a continuous slow feed. It may alternatively be generated as a slow feed in situ by the use of a hydrogen peroxide-producing enzyme system. Such enzyme systems are well known in the art, and include glucose-1-oxidase in the presence of D-glucose, pyranose-2-oxidase or glucose-2-oxidase in the presence of D-glucose, D- and L-amino acid oxidases in the presence of D- and L-methionine, methanol oxidase in the presence of methanol, and diamine oxidases in the presence of histamine. The hydrogen peroxide-generating system may be present in the non-immobilized or immobilized state as with the halogenating enzyme. The hydrogen peroxide may also be generated by chemical reaction, such as by anthraquinone or isopropyl alcohol oxidation processes.

The hydrogen peroxide is present preferably in molar ratio of from about 0.5:1 to about 50:1, most preferably in a ratio of about 1:1 or less with respect to the alkene or alkyne. The molar ratio preferences refer to the average presence of hydrogen peroxide during the reaction. The actual molar ratio will usually vary during the reaction and the molar ratio at any particular time may be above or below the ranges cited. Other suitable oxidizing agents include organic peroxides, such as methyl, ethyl, or butyl peroxides.

Also, a source of two different water-soluble halide salts is required in the reaction mixture. The preferred halide salts are the fluoride, chloride, bromide and iodide salts of the alkali metals, sodium, potassium and lithium. Seawater or other natural brines which contain molar amounts of halide salts can be used. The total concentration of halide ions is usually greater than 2000 mM. The proportion of each halide ion ($X^-$ and $X_1^-$) in the reaction mixture is as follows:

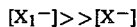

$X^-$ is preferably present at a concentration less than about 10 times, and most preferably less than about 3 times, that required for incorporation of one atom of X into each molecule of product. Thus, $X^-$ will generally be present in 1 to 100 mM amounts. $X_1^-$ is preferably present at a concentration at least 5 times, and more preferably at least about 100 times, that of $X^-$. Thus, $X_1^-$ will usually be present in 0.5 to 3M amounts. $X^-$ represents the halide with the higher standard oxidation potential, as between $X^-$ and $X_1^-$. (The standard oxidation potentials of $I^-$, $Br^-$, $Cl^-$ and $F^-$ are in the order $I^- > Br^- > Cl^- > F^-$).

The reaction is conducted with the pH range of from about 2.2 to about 8.0. The pH of the reaction may be maintained within the desired range by use of a buffering agent. Suitable buffers include sodium or potassium phosphate, gluconate, citrate, formate, and acetate based systems. Other suitable techniques besides buffering may be used for pH control and adjustment.

The reaction is conducted in an aqueous medium. While some of the alkenes and alkynes that can be converted by the process are substantially insoluble in an aqueous medium, the reaction, nevertheless, proceeds satisfactorily under conditions of mixing, or other modes of dispersion, which provide sufficient substrate solubility for the reaction.

The reaction can also be conducted in the presence of aqueous organic solvent mixtures, such as water solutions containing lower aliphatic alcohols, dioxane, dimethylformamide, dimethylsulfoxide or glycerol, in order to increase substrate solubility.

The reaction is preferably conducted under aerobic conditions and in the temperature range of 15° to about 50°, preferably at 20° to about 30°.

As previously indicated, the components of the reaction mixture, namely the alkene or alkyne, the halogenating enzyme, the oxidizing agent, the two different halide ions, and the buffering agent, are simply mixed together in water or mixed aqueous or organic media, and agitated for a period of from about 30 seconds to about 1 hour to obtain the vicinal, heterogeneous dihalogenated products.

The reaction for alkenes is represented by the following equation:

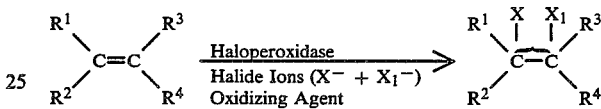

The reaction for alkynes is represented by the following equation:

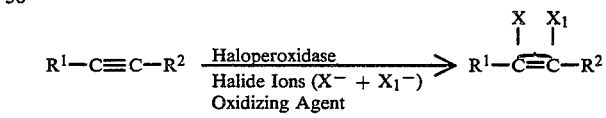

The products were quantitated by gas chromatography (GC) using flame ionization detection (FID). 5 μl of the reaction mixture was injected into a Varian 3700 GC, equipped with a 6 foot×4 mm coiled, glass column packed with Tenax-GC (80/100 mesh). Flow rate through the column was set at 40 ml/minute of helium. The column temperature was operated isothermally (specific temperature given in each example); the injection temperature was set at 240° C.; and the detector temperature was set at 240° C.

The products were identified by gas chromatography-mass spectrometry (GCMS). 10 μl of the reaction mixture was injected into a Finnigan 4021 GCMS, equipped with a 6 foot×4 mm coiled, glass column packed with Tenax-GC (80/100 mesh). Flow rate through the column was set at 30 ml/minute of helium. The column temperature was operated isothermally (specific temperature given in each example); the injection temperature was set at 240° C.; and the jet separator was set at 240° C. The mass spectrometer was operated at 70 eV, electron impact ionization.

Resolution and measurement of certain isomeric, vicinal, heterogeneous dihalogenated products was obtained by capillary gas chromatography-mass spectrometry ($GC^2MS$). The concentrate of the ethyl ether extract of the reaction mixture was injected (10 μl) into a Finnigan 4021 GCMS, equipped with a 25 m×0.25 mm I.D. fused silica capillary column coated with SE-54 (purchased from J and W Scientific Company). Flow rate through the column was set at 2 ml/minute of helium. Samples were injected at 200° C. with a 200:1 split injection. The column temperature was programmed from 60° C. to 200° C. at 5° C./minute. The mass spectrometer was operated at 70 eV, electron impact ionization. The capillary column was directly inserted into the ion source.

The following examples are intended only to further illustrate the invention and are not intended to limit the scope of the invention which is defined by the claims.

EXAMPLE 1

This example demonstrates the control of the ratio of heterogeneous dihalogenated product to homogeneous dihalogenated product by controlling the proportions of the two different halide salts in the reaction. Bromide ion and chloride ion can each be utilized individually by chloroperoxidase.

Potassium bromide, potassium chloride, potassium phosphate buffer at pH 3.5 (10 ml, 0.3M), hydrogen peroxide (4.1 mg; 137 $\mu$l of a 3% solution; 12 mM final) and allyl alcohol (7.0 mg; 12 mM final; $HOCH_2CH=CH_2$; purchased from Aldrich Chemical Company, Milwaukee, WI) were mixed together in a 25 ml Pyrex flask at room temperature and room pressure. The haloperoxidase enzyme, chloroperoxidase (0.4 ml of the final enzyme solution prepared as described in this example from mycelial pads of *C. fumago* (ATCC 16373, NRRL 15272) or 0.1 ml of solution containing *C. fumago* chloroperoxidase obtained by diluting 100-fold the suspension of purified grade enzyme from Sigma Chemical Company, St. Louis, Mo. (Catalog No. C 0887)) was then added. The reaction was concluded 15 minutes after the addition of the last reagent.

The following levels of bromide ion and chloride ion were used:

| Rxn | mM KBr final | mM KCl final | mM Total Halide Ion |
|---|---|---|---|
| A | 3000 | 0 | 3000 |
| B | 1200 | 1200 | 2400 |
| C | 20 | 2000 | 2020 |
| D | 4 | 2000 | 2004 |
| E | 0 | 2000 | 2000 |

The chloroperoxidase was prepared as follows:

Mycelial pads of *Caldariomyces fumago* (ATCC 16373, NRRL 15272) were grown on potato agar slants. Sliced potato (200 g) was cooked in distilled water (500 ml) for 40 minutes and then strained. A solution of glucose (21 g) and agar (20 g) in distilled water (500 ml) was added to the strained solution. The pH was adjusted to 6.8 and the volume was brought to 1 liter with distilled water. The medium was sterilized at 121° C. for 15 minutes.

The organism was inoculated on the potato agar slants, produced in accordance with the above procedure, and was grown for about one week at room temperature. The organism was then used to inoculate a soybean-glucose medium (50 ml). The soybean-glucose medium was prepared by adding, to 1 liter of distilled, extraction process soybean meal (30 g), glucose (30 g), and $CaCO_3$ (7 g). The medium was sterilized at 121° C. for 30 minutes and was then inoculated with the organism after cooling.

The organism was grown for 4–5 days on a rotary shaker at 25° C. 5 ml of this material was used to inoculate a 500 ml Erlenmeyer flask containing 100 ml of a modified Czapek-Dox medium prepared by adding the following to 1 liter of distilled water: $NaNO_3$ (3 g), $KH_2PO_4$ (1 g), KCl (0.5 g), $MgSO_4.7H_2O$ (0.5 g), $FeSO_4.7H_2O$ (10 mg), and glucose (40 g). The medium was sterilized at 121° C. for 20 minutes prior to inoculation with the organism.

The organism was grown under static conditions at room temperature for 5–7 days. The black mycelial pads which formed were collected, rinsed with distilled water, and stored in plastic bags in a freezer at $-10°$ C. for subsequent use.

The halogenating enzyme was prepared by grinding 6 mycelial pads (prepared in accordance with the above procedures) with 60 g acid-washed sand and 60 ml distilled water for 2 minutes in a Virtis 45 homogenizer. The homogenate was centrifuged while cold and the supernatant solution was used as the source of the halogenating enzyme, chloroperoxidase.

The final chloroperoxidase supernatant was filtered through Whatman No. 1 paper at room temperature. The filtrate was concentrated about 10-fold using a rotary film evaporator at reduced pressure and temperature ($<35°$ C.). The concentrate was chilled at 0° C. in an ice bath, and prechilled (0°) ethanol was added until 45% ethanol (v/v) was reached. The mixture was stirred vigorously for 15 minutes, and then centrifuged at $-10°$ C. (at 15,000 g) with a 55-34 rotor in a Sorval RC-5 Superspeed for 15 minutes. The black sediment was discarded. To the centrifugate, cooled at 0° C., was added additional prechilled ethanol to give 65% ethanol (v/v). The mixture was slowly stirred for 30 minutes at 0° C., and then centrifuged as before. The centrifugate was discarded, and the precipitate containing the chloroperoxidase activity was dissolved in 1 ml of 0.05M potassium phosphate buffer (pH 7). The enzyme solution was stored at $-20°$ C.

The products were quantitated by gas chromatography (GC) using flame ionization detection (FID). 5 $\mu$l of the reaction mixture was injected into a Varian 3700 GC, equipped with a 6 foot $\times$ 4 mm coiled, glass column packed with Tenax-GC (80/100 mesh). Flow rate through the column was set at 40 ml/minute of helium. The column temperature was set at 190° C., isothermal; the injection temperature was set at 240° C.; and the detector temperature was set at 240° C.

The products were identified by gas chromatography-mass spectrometry (GCMS). 10 $\mu$l of the reaction mixture was injected into a Finnigan 4021 GCMS, equipped with a 6 foot $\times$ 4 mm coiled, glass column packed with Tenax-GC (80/100 mesh). Flow rate through the column was set at 30 ml/minute of helium. The column temperature was set at 190° C., isothermal; the injection temperature was set at 240° C.; and the jet separator was set at 240° C.; the mass spectrometer was operated at 70 eV, electron impact ionization.

Seven products were detected.

One product had a GC retention time of 6 minutes and showed the mass spectrum diagnostic for 2,3-dichloro-1-propanol:molecular mass ion not detected; major fragment mass ions at mass 92 and 94 (3:1 in intensity; loss of HCl from molecular ion), and at mass 62 and 64 (3:1 in intensity; the $CH_2CHCl^+$ ion). This product had an identical GC retention time and mass spectrum with that of an authentic sample of 2,3-dichloro-1-propanol (purchased from Aldrich Chemical Company).

Two other products had GC retention times of 7 and 8 minutes, and showed the mass spectra diagnostic for chloropropanediols. The product having a 7 minute retention time was identified as 1-chloro-2,3-propanediol:molecular mass ion not detected; major fragment mass ions at mass 79 and 81 (3:1 in intensity; loss of CH₂OH from the molecular ion), and at mass 61 (loss of CH₂Cl from molecular ion). The product having an 8 minute retention time was identified as 2-chloro-1,3-propanediol:molecular mass ion not detected; major fragment mass ions at mass 92 and 94 (3:1 in intensity; loss of H₂O from molecular ion), and at mass 62 and 64 (3:1 in intensity; the CH₂CHCl+ ion).

Another product had a GC retention time of 10 minutes, and showed the mass spectrum diagnostic for bromochloro-1-propanol:molecular mass ion at mass 172, 174 and 176 (3:4:1 in intensity) indicating one chlorine atom and one bromine atom on the molecule; major fragment mass ions at mass 136 and 138 (1:1 in intensity; loss of HCl from molecular ion), at mass 106 and 108 (1:1 in intensity; the CHCH₂Br+ ion), and at mass 92 and 94 (3:1 in intensity; loss of HBr from molecular ion).

Two other products had GC retention time of 11 and 12 minutes, and showed the mass spectra diagnostic for bromopropanediols. The product having a 11 minute retention time was identified as 1-bromo-2,3-propanediol:molecular ion not detected; major fragment mass ions at mass 123 and 125 (1:1 in intensity; loss of CH₂OH from molecular ion), and at mass 61 (loss of CH₂Br from molecular ion). The product having a 12 minute retention time was identified as 2-bromo-1,3-propandiol:molecular mass ion not detected; major fragment mass ions at mass 136 and 138 (1:1 in intensity; loss of H₂O from molecular ion), and at mass 106 and 108 (1:1 in intensity; the CH₂CHBr+ ion).

A final product had a GC retention time of 16 minutes and showed the mass spectrum diagnostic for 2,3-dibromo-1-propanol:molecular mass ion at mass 216, 218 and 220 (1:2:1 in intensity) indicating 2 bromine atoms on the molecule; major fragment mass ions at 137 and 139, and 136 and 138 (both sets 1:1 in intensity; loss of Br and HBr, respectively, from molecular ion) and at mass 106 and 108 (1:1 in intensity; the CH₂CHBr+ ion). This product had an identical GC retention time and mass spectrum with that of an authentic samples of 2,3-dibromo-1-propanol (purchased from Aldrich Chemical Company).

The following summarizes the products obtained:

| Product | % of Total Yield | | | | |
|---|---|---|---|---|---|
| | Rxn A | Rxn B | Rxn C | Rxn D | Rxn E |
| OH Cl Br<br>\| \| \|<br>CH₂—CH—CH₂ | 0 | 69 | 95 | 73 | 0 |
| OH Cl Cl<br>\| \| \|<br>CH₂—CH—CH₂ | 0 | 0 | 0 | 24 | 91 |
| OH OH Cl<br>\| \| \|<br>CH₂—CH—CH₂<br>OH Cl OH<br>\| \| \|<br>CH₂—CH—CH₂ | 0 | 0 | 0 | 2 | 9 |
| OH OH Br<br>\| \| \|<br>CH₂—CH—CH₂<br>OH Br OH<br>\| \| \|<br>CH₂—CH—CH₂ | 1 | 1 | 0 | 0 | 0 |
| OH Br Br<br>\| \| \|<br>CH₂—CH—CH₂ | 99 | 31 | 5 | 1 | 0 |
| Total Yield | 21.7 mg | 15.2 mg | 13.9 mg | 9.7 mg | 5.4 mg |

Reaction C thus demonstrates the proportions of the two halide ion levels needed for this heterogeneous, dihalogenated product reaction.

Further analysis of the bromochloro-1-propanol product was made using capillary gas chromatography-mass spectrometry (GC²MS). The reaction mixture was extracted with ethyl ether, and this extract when concentrated was injected (10 μl) into a Finnigan 4021 GCMS, equiped with a 25 m×0.25 mm I.D. fused silica capillary column coated with SE-54. Flow rate through the column was set at 2 ml/minute of helium. Sample was injected at 200° C. with a 200:1 split injection. The column temperature was programmed from 60° C. to 150° C. at 5° C./minute. The mass spectrometer was operated at 70 eV, electron impact ionization. The capillary column was directly inserted into the ion source.

2-Bromo-3-chloro-1-propanol had a GC² retention time of 3.6 minutes, and showed the following diagnostic mass spectrum: molecular mass ion not detected; major fragment mass ions at mass 136 and 138 (1:1 in intensity; loss of HCl from molecular ion), mass 106 and 108 (1:1 in intensity; the CH₂CHBr+ ion), and at mass 57 (loss of HBrCl from molecular ion).

3-Bromo-2-chloro-1-propanol had a GC² retention time of 3.8 minutes, and showed the following diagnostic mass spectrum: molecular mass ion at mass 172, 174 and 176 (3:4:1 in intensity) indicating one chlorine atom and one bromine atom on the molecule; major fragment mass ions at mass 93 and 95 (3:1 in intensity; loss of Br from molecular ion), at mass 92 and 94 (3:1 in intensity; loss of HBr from molecular ion), and at mass 57 (loss of HBrCl from molecular ion).

The ratio of product formed was 1:1.2; 2-bromo-3-chloro-1-propanol:3-bromo-2-chloro-1-propanol.

In addition, the bromochloro-1-propanol products were converted to epichlorohydrin and epibromohydrin by addition of lime to the aqueous reaction mixture until the pH was greater than 10. Identity of epichlorohydrin and epibromohydrin was confirmed by gas chromatography-mass spectrometry comparison with authentic samples (purchased from Aldrich Chemical Company).

Further, the bromochloro-1-propanol products were converted to epichlorohydrin and epibromohydrin by addition of Flavobacterium sp. whole cells to the aqueous reaction mixture, as set forth in U.S. Pat. No. 4,247,641 (Neidleman et al, 1981).

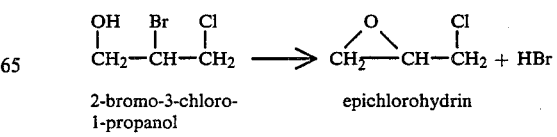

2-bromo-3-chloro-1-propanol    epichlorohydrin

-continued

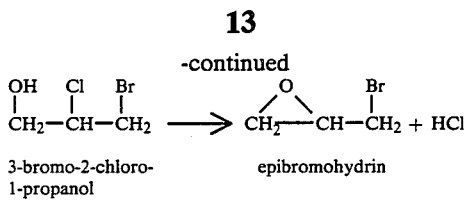

3-bromo-2-chloro-1-propanol → epibromohydrin + HCl

EXAMPLE 2

This example demonstrates control of the ratio of heterogeneous dihalogenated product to homogeneous dihalogenated product by adjusting the proportions of the two different halide salts in the reaction. Bromide ion can be utilized by lactoperoxidase individually but chloride ion cannot.

The procedure of Example 1 was followed, except (1) sodium chloride was substituted for potassium chloride, (2) lactoperoxidase (purchased from Sigma Chemical Company, St. Louis, MO; Catalog No. L-7129; 0.5 ml used per reaction) was substituted for chloroperoxidase, and (3) the buffer pH was set at 6.5 rather than 3.5.

The following levels of bromide ion and chloride ion were used:

| Rxn | mM KBr final | mM NaCl final | mM Total Halide Ion |
|-----|--------------|---------------|---------------------|
| A   | 3000         | 0             | 3000                |
| B   | 1200         | 1200          | 2400                |
| C   | 20           | 2000          | 2020                |
| D   | 4            | 2000          | 2004                |
| E   | 0            | 2000          | 2000                |

Analysis of products by GC and GCMS was as outlined in Example 1.

The following summarizes the products obtained as a function of halide concentrations in the reaction mixture:

| Product | % of Total Yield | | | | |
|---|---|---|---|---|---|
| | Rxn A | Rxn B | Rxn C | Rxn D | Rxn E |
| OH Cl Br<br>CH$_2$—CH—CH$_2$ | 0 | 61 | 93 | 98 | 0 |
| OH Cl Cl<br>CH$_2$—CH—CH$_2$ | 0 | 0 | 0 | 0 | 0 |
| OH OH Cl<br>CH$_2$—CH—CH$_2$ | 0 | 0 | 0 | 0 | 0 |
| OH OH Br<br>CH$_2$—CH—CH$_2$ | 1 | 0 | 0 | 0 | 0 |
| OH Br Br<br>CH$_2$—CH—CH$_2$ | 98 | 49 | 7 | 2 | 0 |
| Total Yield | 20.8 mg | 18.7 mg | 14.0 mg | 6.2 mg | 0 mg |

Reactions C and D thus demonstrate the proportions of the two halide ion levels needed for this heterogeneous, dihalogenated product reaction.

EXAMPLE 3

The procedure of Example 1 was followed, except potassium iodide was substituted for potassium bromide. Chloride ion and iodide ion can each be utilized individually by chloroperoxidase.

The following level of chloride ion and iodide ion was used:

| mM KI final | mM KCl final | mM Total Halide Ion |
|-------------|--------------|---------------------|
| 20          | 2000         | 2020                |

Analysis of products by GC and GCMS was as outlined in Example 1. The GC column temperature was set at 210° C., isothermal. Seven products were detected.

One product had a GC retention time of 28 minutes and showed the mass spectrum diagnostic for 2,3-diiodo-1-propanol:molecular mass ion not detected; major fragment mass ions at mass 254 (the $I_2^+$ ion), at mass 185 (loss of I from molecular ion), at mass 127 (the $I^+$ ion), and at mass 57 (loss $HI_2$ from molecular ion)

Two other products had GC retention times of 9 and 11 minutes, and showed the mass spectra diagnostic for iodopropanediols. The products having a 9 minute retention time was identified as 1-iodo-2,3-propanediol:molecular mass ion at mass 202; major fragment mass ions at mass 171 (loss of $CH_2OH$ from molecular ion) and at mass 75 (loss of I from molecular ion). The product having a 11 minute retention time was identified as 2-iodo-1,3-propanediol:molecular mass ion at mass 202; major fragment mass ions at mass 154 (loss of $CH_2OH$+OH from molecular ion) at mass 127 (the $I^+$ ion) and at mass 75 (loss of I from molecular ion).

Another product had a GC retention time of 7 minutes, and showed the mass spectrum diagnostic for chloroiodo-1-propanol:molecular mass ion at mass 220 and 222 (3:1 in intensity) indicating one chlorine atom on the molecule; major fragment mass ions at mass 127 (the $I^+$ ion), at mass 93 and 95 (3:1 in intensity; loss of I from molecular ion), and at mass 57 (loss of HClI from molecular ion).

Another product had a GC retention time of 2 minutes and showed the mass spectrum diagnostic for 2,3-dichloro-1-propanol:molecular mass ion not detected; major fragment mass ions at mass 92 and 94 (3:1 in intensity; loss of HCl from molecular ion), and at mass 62 and 64 (3:1 in intensity; the $CH_2CHCl^+$ ion). This product had an identical GC retention time and mass spectrum with that of an authentic sample of 2,3-dichloro-1-propanol (purchased from Aldrich Chemical Company).

And two other products had GC retention times of 3 and 4 minutes, and showed the mass spectra diagnostic for chloropropanediols. The product having a 3 minute retention time was identified as 1-chloro-2,3-propanediol:molecular mass ion not detected; major fragment mass ions at mass 79 and 81 (3:1 in intensity; loss of $CH_2OH$ from the molecular ion), and at mass 61 (loss of $CH_2Cl$ from molecular ion). The product having an 8 minute retention time was identified as 2-chloro-1,3-propanediol:molecular mass ion not detected; major fragment mass ions at mass 92 and 94 (3:1 in intensity; loss of $H_2O$ from molecular ion), and at mass 62 and 64 (3:1 in intensity; the $CH_2CHCl^+$ ion).

Molecular iodine ($I_2$) was also formed.

The following summarizes the products obtained:

| Product | % of Total Yield |
|---|---|
| OH I Cl<br>\|  \|  \|<br>CH₂—CH—CH₂ | 46 |
| OH Cl Cl<br>\|  \|  \|<br>CH₂—CH—CH₂ | 17 |
| OH OH Cl<br>\|  \|  \|<br>CH₂—CH—CH₂ | 8 |
| OH OH I<br>\|  \|  \|<br>CH₂—CH—CH₂ | 21 |
| OH I I<br>\|  \|  \|<br>CH₂—CH—CH₂ | 8 |
| Total Yield = | 5.3 mg |

Further analysis of the chloroiodo-1-propanol product was made using capillary gas chromatography-mass spectrometry ($GC^2MS$) as described in Example 1.

2-Chloro-3-iodo-1-propanol had a $GC^2$ retention time of 6.4 minutes, and showed the following diagnostic mass spectrum: molecular mass ion at mass 220 and 222 (3:1 in intensity) indicating one chlorine atom on the molecule; major fragment mass ions at mass 127 (the I+ ion), at mass 93 and 95 and (3:1 in intensity; loss of I from molecular ion), and at mass 57 (loss of HClI from molecular ion).

3-Chloro-2-iodo-1-propanol had a $GC^2$ retention time of 6.2 minutes, and showed the following diagnostic mass spectrum: molecular mass ion at mass 220 and 222 (3:1 in intensity) indicating one chlorine atom on the molecule; major fragment mass ions at mass 93 and 95 (3:1 in intensity; loss of I from molecular ion), and at mass 57 (loss of HClI from molecular ion).

The ratio of product formed was 1:1; 2-chloro-3-iodo-1-propanol: 3-chloro-2-iodo-1-propanol.

In addition, the chloroiodo-1-propanols were converted to epichlorohydrin and epiiodohydrin by addition of lime to the aqueous reaction mixture until the pH was greater than 10. Identity of epichlorohydrin and epiiodohydrin was confirmed by gas chromatography-mass spectrometry comparison with authentic samples (purchased from Aldrich Chemical Company).

Further, the chloroiodo-1-propanols were converted to epichlorohydrin and epiiodohydrin by addition of Flavobacterium sp. whole cells to the aqueous reaction mixture, as set forth in U.S. Pat. No. 4,247,641 (Neidleman et al, 1981).

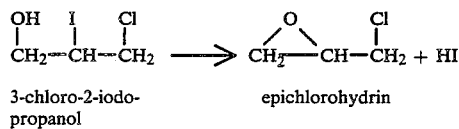

3-chloro-2-iodo-propanol → epichlorohydrin + HI

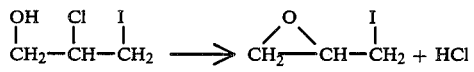

2-chloro-3-iodo-1-propanol → epiiodohydrin + HCl

EXAMPLE 4

The procedure of Example 1 was followed, except (1) potassium iodide and sodium fluoride were substituted for potassium bromide and potassium chloride, (2) horseradish peroxidase (2mg; purchased from Sigma Chemical Company, Catalog No. P-8375) was substituted for chloroperoxidase, and (3) the buffer pH was set at 6.5 rather than 3.5. Iodine ion can be utilized by horseradish peroxidase individually but fluoride ion cannot.

The following level of iodide ion and fluoride ion was used:

| mM KI final | mM NaF final | mM Total Halide Ion |
|---|---|---|
| 100 | 2000 | 2100 |

Analysis of products by GC and GCMS was as outlined in Example 1. The GC column temperature was set at 210° C., isothermal. Five products were detected.

One product had a GC retention time of 28 minutes and showed the mass spectrum diagnostic for 2,3-diiodo-1-propanol: molecular mass ion not detected; major fragment mass ions at mass 254 (the $I_2$+ ion), at mass 185 (loss of I from molecular ion), at mass 127 (I+ ion), and at mass 57 (loss of $HI_2$ from molecular ion).

Two other products had GC retention times of 9 and 11 minutes, and showed the mass spectra diagnostic for iodopropanediols. The product having a 4 minute retention time was identified as 1-iodo-2,3-propanediol: molecular mass ion at mass 202; major fragment mass ions at mass 171 (loss of $CH_2OH$ from molecular ion) and at mass 75 (loss of I from molecular ion). The product having a 6 minute retention time was identified as 2-iodo-1,3-propanediol: molecular mass ion at mass 202; major fragment mass ions at mass 154 (loss of $CH_2OH$+OH from molecular ion) at mass 127 (the I+ ion) and at mass 75 (loss of I from molecular ion).

Another product had a GC retention time of 5 minutes, and showed the mass spectrum diagnostic for 2-fluoro-3-iodo-1-propanol: molecular mass ion at mass 204; major fragment mass ions at mass 127 (the I+ ion), and at mass 77 (loss of I from molecular ion).

And another product had a GC retention time of 4 minutes, and showed the diagnostic mass spectrum for 3-fluoro-2-iodo-1-propanol: molecular mass ion at mass 204; major fragment mass ions at mass 154 (the $CH_2CHI$+ ion) at mass 127 (the I+ ion), and at mass 77 (loss of I from molecular ion).

Molecular iodine ($I_2$) was also formed.

The following summarizes the products obtained:

| Product | % of Total Yield |
|---|---|
| OH F I<br>\|  \|  \|<br>CH₂—CH—CH₂ | 8 |
| OH I F<br>\|  \|  \|<br>CH₂—CH—CH₂ | 9 |
| OH OH I<br>\|  \|  \|<br>CH₂—CH—CH₂ | 52 |
| OH I I<br>\|  \|  \|<br>CH₂—CH—CH₂ | 31 |

| Product | % of Total Yield |
|---|---|
| Total Yield = | 4.3 mg |

This procedure thus provides a method for the production of 2-fluoro-3-iodo-1-propanol and 3-fluoro-2-iodo-1-propanol, both of which are new compositions of matter. 3-Fluoro-2-iodo-1-propanol may be treated with a base such as lime or caustic soda, as shown below, to form epifluorohydrin, an epoxide having known utility in the polymer industry. 2-Fluoro-3-iodo-1-propanol may be converted by catalytic hydrogenation, as shown below, to form propylenefluorohydrin, the structure of which indicates utility as an intermediate for producing fluorinated esters useful in the polymer industry.

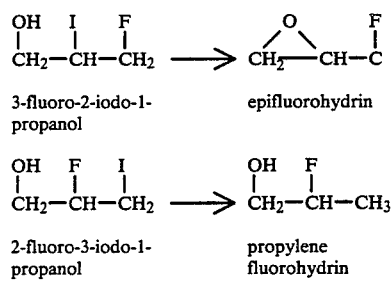

3-fluoro-2-iodo-1-propanol → epifluorohydrin 2-fluoro-3-iodo-1-propanol → propylene fluorohydrin

EXAMPLE 5

The procedure of Example 4 was followed, except potassium bromide was substituted for sodium fluoride. Iodide ion can be utilized by horseradish peroxidase individually but bromide ion cannot.

The following level of bromide ion and iodide ion was used.

| mM KI final | mM KBr final | mM Total Halide Ion |
|---|---|---|
| 20 | 150 | 170 |

Analysis of products by GC and GCMS was as outlined in Example 1. The GC column temperature was set at 220° C., isothermal. Four products were detected.

One product had a GC retention time of 23 minutes and showed the mass spectrum diagnostic for 2,3-diiodo-1-propanol: molecular mass ion not detected; major fragment mass ions at mass 254 (the $I_2^+$ ion), at mass 185 (loss of I from molecular ion), at mass 127 (the $I^+$ ion), and at mass 57 (loss of $HI_2$ from molecular ion).

Two other products had GC retention times 6 and 8 minutes, and showed the mass spectra diagnostic for iodopropanediols. The product having a 6 minute retention time was identified as 1-iodo-2,3-propanediol: molecular mass ion at mass 202; major fragment mass ions at mass 171 (loss of $CH_2OH$ from molecular ion) and at mass 75 (loss of I from molecular ion). The product having an 8 minute retention time was identified as 2-iodo-1,3-propanediol: molecular mass ion at mass 202; major fragment mass ions at mass 154 (loss of $CH_2OH$+OH from molecular ion) at mass 127 (the $I^+$ ion) and at mass 75 (loss of I from molecular ion).

Another product had a GC retention time of 13 minutes, and showed the mass spectrum diagnostic for bromoiodo-1-propanol: molecular mass ion at mass 264 and 266 (1:1 in intensity) indicating one bromine atom on the molecule; major fragment mass ions at mass 206 and 208 (1:1 in intensity; the $IBr^+$ ion), at mass 137 and 139 (1:1 in intensity; loss of I from the molecule), and at mass 127 (the $I^+$ ion).

Molecular iodine ($I_2$) was also formed.

When the same reaction was run with a final KBr concentration of 2000 mM rather than 150 mM, the total yield increased to 5.2 mg, the percentage of the bromo-iodo product increased to 42, the percentage of the diiodo product increased to 28, and the percentage of the iodo-diol product decreased to 30.

Further analysis of the bromoiodopropanol product was made using capillary gas chromatography-mass spectrometry ($GC^2MS$) as described in Example 1.

2-Bromo-3-iodo-1-propanol had a $GC^2$ retention time of 8.8 minutes and showed the following diagnostic mass spectrum: molecular mass ion at mass 264 and 266 (1:1 in intensity) indicating one bromine atom on the molecule; major fragment mass ions at mass 233 and 235 (1:1 in intensity; loss of $CH_2OH$ from molecular ion), at mass 206 and 208 (1:1 in intensity; the $IBr^+$ ion), at mass 137 and 139 (1:1 in intensity; loss of I from molecular ion), at mass 127 (the $I^+$ ion), at mass 106 and 108 (1:1 in intensity; the $CH_2CHBr^+$ ion), and at mass 57 (loss of HIBr from molecular ion).

3-Bromo-2-iodo-1-propanol had a $GC^2$ retention time of 8.6 minutes, and showed the following diagnostic mass spectrum: molecular mass ion at mass 264 and 266 (1:1 in intensity) indicating one bromine atom on the molecule; major fragment mass ions at mass 233 and 235 (1:1 in intensity; loss of $CH_2OH$ from molecular ion), at mass 206 and 208 (1:1 in intensity; the $IBr^+$ ion), at mass 154 (the $CH_2CHI^+$ ion), at mass 137 and 139 (1:1 in intensity; loss of I from molecular ion), and at mass 57 (the loss of HIBr from molecular ion).

This procedure thus provides a method for the production of 2-bromo-3-iodo-1-propanol and 3-bromo-2-iodo-1-propanol, both of which are new compositions of matter.

In addition, the bromoiodo-1-propanols were converted to epibromohydrin and epiiodohydrin by addition of lime or addition of Flavobacterium sp. whole cells to the reaction mixture. Identity of epibromohydrin and epiiodihydrin was confirmed by gas chromatography-mass spectrometry comparison with authentic samples (purchased from Aldrich Chemical Company).

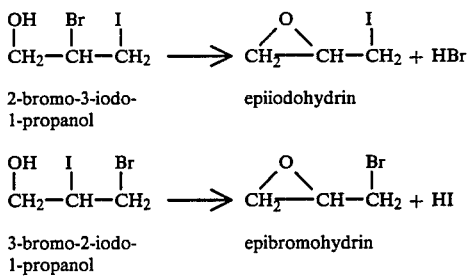

2-bromo-3-iodo-1-propanol → epiiodohydrin + HBr 3-bromo-2-iodo-1-propanol → epibromohydrin + HI This procedure thus provides a method for the production of 2-bromo-3-iodo-1-propanol and 3-bromo-2-iodo-1-propanol, both of which are new compositions of matter. 2-Bromo-3-iodo-1-propanol provides a useful intermediate for forming epiiodohydrin, as shown above, a known epoxide useful in polymers. 3-Bromo-2-iodo-1-propanol similarly provides a useful intermediate for forming epibromohydrin, as shown above, also a known epoxide useful in polymers.

EXAMPLE 6

The procedure of Example 2 was followed, except: (1) the final potassium bromide and sodium chloride levels were 20 mM and 2000 mM, respectively, and (2) in situ generation of hydrogen peroxide was made by adding β-D-glucose (25 mg) and glucose-1-oxidase (0.05 ml; purchased from Sigma Chemical Company, Catalog No. G-6500). The reaction was allowed to proceed for 2 hours.

The following summarizes the products obtained:

| Product | % of Total Yield |
|---|---|
| OH Cl Br<br>\|   \|   \|<br>CH₂CH—CH₂ | 91 |
| OH Br Br<br>\|   \|   \|<br>CH₂—CH—CH₂ | 9 |
| Total Yield = | 8.6 mg |

EXAMPLE 7

The procedure of Example 1 was followed, except 2-butene-1,4-diol (11 mg; 12 mM final; HOCH₂CH=CHCH₂OH; purchased from Aldrich Chemical Company) was substituted for allyl alcohol.

The following level of bromide ion and chloride ion was used:

| mM KBr | mM KCl | mM Total Halide Ion |
|---|---|---|
| 20 | 2000 | 2020 |

Analysis of products by GC and GCMS was as outlined in Example 1. The GC column temperature was set at 210° C., isothermal. Two products were detected.

One product had a GC retention time of 19 minutes and showed the mass spectrum diagnostic for 2,3-dibromo-1,4-butanediol: molecular mass ion not detected; major fragment mass ions at mass 198, 200 and 202 (1:2:1 in intensity; loss of CH₂OH+OH from molecular ion), mass 167 and 169 (1:1 in intensity; loss of Br from molecular ion), and at mass 149 and 151 (1:1 in intensity; loss of Br+H₂O from molecular ion).

The other product had a GC retention time of 15 minutes and showed the mass spectrum diagnostic for 2-bromo-3-chloro-1,4-butanediol: molecular mass ion at mass 202, 204 and 206 (3:4:1 in intensity) indicating one bromine atom and one chlorine atom on the molecule; major fragment mass ions at mass 154, 156 and 158 (3:4:1 in intensity; loss of CH₂OH+OH from molecular ion), at mass 167 and 169 (1:1 in intensity; loss of Cl from molecular ion), at mass 123 and 125 (3:1 in intensity; loss of Br from molecular ion), and at mass 105 and 107 (3:1 in intensity; loss of Br+H₂O from molecular ion).

The following summarizes the products obtained:

| Product | % of Total Yield |
|---|---|
| OH Cl Br OH<br>\|   \|   \|   \|<br>CH₂—CH—CH—CH₂ | 83 |
| OH Br Br OH<br>\|   \|   \|   \|<br>CH₂—CH—CH—CH₂ | 17 |
| Total Yield = | 10.6 mg |

This procedure thus provides a method for the production of 2-bromo-3-chloro-1,4-butanediol, a new composition of matter. As shown below, 2-bromo-3-chloro-1,4-butanediol may be reacted over an extended time with a base such as lime or caustic soda to form butadiene diepoxide, an epoxide having known utility in the polymer industry.

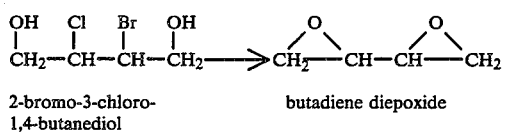

2-bromo-3-chloro-1,4-butanediol     butadiene diepoxide

When the procedure of this example is followed with 20 mM KI in place of 20 mM KBr, the 2-chloro-3-iodo-1,4-butanediol is obtained. When the procedure is carried out with 20 mM KI and 2000 mM KBr, the 2-bromo-3-iodo-1,4-butanediol is obtained. Similarly, when the procedure is followed with 2000 mM KF and 20 mM KI, the 2-fluoro-3-iodo-1,4-butanediol is obtained. When the procedure is carried out with 2000 mM KF and 20 mM KBr, the 2-fluoro-3-bromo-1,4-butanediol is obtained. Finally, when the procedure is carried out with 2000 mM KF and 20 mM KCl, the 2-fluoro-3-chloro-1,4-butanediol is obtained. All of these vicinal, heterogeneously dihalogenated 1,4-butanediols can be converted to butadiene diepoxide in the same manner as 2-bromo-3-chloro-1,4-butanediol.

EXAMPLE 8

The procedure of Example 7 was followed except 2-butyne-1,4-diol (10.3 mg; 12 mM final; HOCH₂C≡CCH₂OH; purchased from Aldrich Chemical Company) was substituted for 2-butene-1,4-diol.

Two products were detected. The GC column temperature was set at 210° C., isothermal.

One product had a GC retention time of 13 minutes, and showed the mass spectrum diagnostic for 2-bromo-3-chloro-2-butene-1,4-diol: molecular ion at mass 200, 202 and 204 (3:4:1 in intensity) indicating one bromine atom and one chlorine atom on the molecule; major fragment mass ions at mass 182, 184 and 186 (3:4:1 in intensity; loss of H₂O from molecular ion), at mass 165 and 167 (1:1 in intensity; loss of Cl from molecular ion), and at mass 147 and 149 (1:1 in intensity; loss of Cl+H₂O from molecular ion.

And the other product had a GC retention time of 17 minutes, and showed the mass spectrum diagnostic for 2,3-dibromo-2-butene-1,4-diol: molecular mass ion at mass 244, 246 and 248 (1:2:1 in intensity) indicating two bromine atoms on the molecule; major fragment mass ions at mass 226, 228, 230 (1:2:1 in intensity; loss of H₂O from molecular ion), at mass 165 and 167 (1:1 in intensity; loss of Br from molecular ion), at mass 147 and 149 (1:1 in intensity: loss of Br+H₂O from molecular ion).

The following summarizes the products obtained:

| Product | % of Total Yield |
|---|---|
| $\underset{CH_2-C=C-CH_2}{\overset{OH\ \ \ Cl\ \ \ Br\ \ \ OH}{|\ \ \ \ |\ \ \ \ |\ \ \ \ |}}$ | 86 |
| $\underset{CH_2-C=C-CH_2}{\overset{OH\ \ \ Br\ \ \ Br\ \ \ OH}{|\ \ \ \ |\ \ \ \ |\ \ \ \ |}}$ | 14 |
| Total Yield = | 6.9 mg |

EXAMPLE 9

The procedure of Example 7 was followed, except ethylene was substituted for 2-butene-1,4-diol.

Ethylene ($CH_2=CH_2$; purchased from Matheson Gas Products, Lyndhurst, NJ), a gaseous alkene, was slowly (10 ml/min) and continuously bubbled through the reaction mixture. After 15 minutes, the haloperoxidase enzyme chloroperoxidase (0.4 ml), was then added. Finally hydrogen peroxide (4.1 mg; 12 mM final) was added. The reaction was concluded 15 minutes after the addition of the last reagent.

Five products were detected. The GC column temperature was set at 170° C., isothermal.

One product had a GC retention time of 7 minutes and showed the mass spectrum diagnostic for 1,2-dibromo ethane: molecular mass ion at mass 186, 188 and 190 (1:2:1 in intensity) indicating two bromine atoms on the molecule; major fragment mass ions at 107 and 109 (1:1 in intensity; loss of Br from molecular ion), and at mass 93 and 95 (1:1 in intensity; the $CH_2Br^+$ ion). This product had an identical GC retention time and mass spectrum with that of an authentic sample of 1,2-dibromo ethane (purchased from Aldrich Chemical Company).

Another product had a GC retention time of 5 minutes and showed the mass spectrum diagnostic for 2-bromo ethanol; molecular mass ion at mass 124 and 126 (1:1 in intensity) indicating one bromine atom on the molecule; major fragment mass ions at mass 123 and 125 (1:1 in intensity; loss of H from molecular ion) and at mass 93 and 95 (1:1 in intensity; the $CH_2Br^+$ ion).

A third product had a GC retention time of 4 minutes and showed the mass spectrum diagnostic for 1-bromo-2-chloro ethane: molecular mass ion at mass 142, 144 and 146 (3:4:1 in intensity) indicating one bromine atom and one chlorine atom on the molecule; major fragment mass ions at mass 93 and 95 (1:1 in intensity; the $CH_2Br^+$ ion), at mass 79 and 81 (1:1 in intensity; the $Br^+$ ion) and at mass 63 and 65 (3:1 in intensity; loss of Br from molecular ion).

Another product had a GC retention time of 2 minutes and showed the mass spectrum diagnostic for 1,2-dichloro ethane: molecular mass ion at mass 98, 100 and 102 (10:6:1 in intensity) indicating two chlorine atoms on the molecule; major fragment mass ions at mass 62 and 64 (3:1 in intensity; loss of HCl from molecular ion), and at mass 49 and 51 (3:1 in intensity; the $CH_2Cl^+$ ion). This product had an identical GC retention time and mass spectrum with that of an authentic sample of 1,2-dichloro ethane (purchased from Aldrich Chemical Company).

And the other product had a GC retention time of 3 minutes and showed the mass spectrum diagnostic for 2-chloro ethanol: molecular mass ion at mass 80 and 82 (3:1 in intensity) indicating one chlorine atom on the molecule; major fragment mass ions at mass 49 and 51 (3:1 in intensity; the $CH_2Cl^+$ ion), and at mass 44 (loss of HCl from molecular ion).

The following summarizes the products obtained:

| Product | % of Total Yield |
|---|---|
| $\underset{CH_2-CH_2}{\overset{Cl\ \ \ \ Br}{|\ \ \ \ \ |}}$ | 28 |
| $\underset{CH_2-CH_2}{\overset{Br\ \ \ \ Br}{|\ \ \ \ \ |}}$ | 19 |
| $\underset{CH_2-CH_2}{\overset{OH\ \ \ \ Br}{|\ \ \ \ \ |}}$ | 22 |
| $\underset{CH_2-CH_2}{\overset{OH\ \ \ \ Cl}{|\ \ \ \ \ |}}$ | 14 |
| $\underset{CH_2-CH_2}{\overset{Cl\ \ \ \ Cl}{|\ \ \ \ \ |}}$ | 17 |
| Total Yield = | 6.5 mg |

EXAMPLE 10

The procedure of Example 9 was followed, except (1) lactoperoxidase (0.5 ml) was substituted for chloroperoxidase, (2) potassium iodide was substituted for potassium bromide, and (3) the buffer pH was set at 6.5 rather than 3.5.

The following level of chloride ion and iodide ion was used:

| mM KI final | mM KCl final | mM Total Halide Ion |
|---|---|---|
| 20 | 2000 | 2020 |

Three products were detected. The GC column temperature was set at 180° C., isothermal.

One product had a GC retention time of 9 minutes and showed the mass spectrum diagnostic for 1-chloro-2-iodo ethane: molecular mass ion at mass 190 and 192 (3:1 in intensity) indicating one chlorine atom on the molecule; major fragment mass ions at mass 155 (loss of Cl from molecular ion), at mass 127 (the $I^+$ ion), and at mass 63 and 65 (3:1 in intensity; loss of I from molecular ion).

Another product had a GC retention time of 15 minutes and showed the mass spectrum diagnostic for 1,2-diiodo ethane: molecular mass ion at mass 282; major fragment mass ions at mass 254 (the $I_2^+$ ion), at mass 155 (loss of I from molecular ion), and at mass 127 (the $I^+$ ion).

And the other product had a GC retention time of 10 minutes and showed the mass spectrum diagnostic for 2-iodo ethanol: molecular mass ion at mass 172; major fragment mass ions at mass 142 (the $CH_2I^+$ ion), and at mass 127 (the $I^+$ ion).

Molecular iodine was also detected.

The following summarizes the products obtained:

| Product | % of Total Yield |
|---|---|
| $\underset{CH_2\ \ CH_2}{\overset{Cl\ \ \ \ I}{|\ \ \ \ \ |}}$ | 38 |

-continued

| Product | % of Total Yield |
|---|---|
| OH   I<br> \|     \|<br>CH$_2$ CH$_2$ | 47 |
| I    I<br>\|    \|<br>CH$_2$ CH$_2$ | 15 |
| Total Yield = | 4.3 mg |

EXAMPLE 11

The procedure of Example 2 was followed, except allyl chloride (9.1 mg, 12 mM final; ClCH$_2$CH=CH$_2$; purchased from Aldrich Chemical Company) was substituted for allyl alcohol.

The following level of bromide ion and chloride ion was used:

| mM KBr | mM KCl | mM Total Halide Ion |
|---|---|---|
| 20 | 2000 | 2020 |

Analysis of products by GC and GCMS was as outlined in Example 1. The GC column temperature was set at 190° C., isothermal. Four products were detected.

One product had a GC retention time of 8 minutes and showed the mass spectrum diagnostic for bromochloro-1-chloropropane: molecular mass ion at mass 190, 192 and 194 (6:10:5 in intensity) indicating 1 bromine atom and 2 chlorine atoms on the molecule; major fragment mass ions at mass 155, 157 and 159 (3:4:1 in intensity; loss of cl from molecular ion), at mass 141, 143 and 145 (3:4:1 in intensity; loss of CH$_2$Cl from molecular ion), at mass 111, 113 and 115 (10:6:1 in intensity; loss of Br from molecular ion), at mass 93 and 95 (1:1 in intensity; the CH$_2$Br+ ion), and at mass 49 and 51 (3:1 in intensity; the CH$_2$Cl+ ion).

Another product had a GC retention time of 15 minutes and showed the mass spectrum diagnostic for 1,2-dibromo-3-chloropropane: molecular mass ion not detected; major fragment mass ions at mass 185, 187 and 189 (1:2:1 in intensity; loss of CH$_2$Cl from molecular ion), at mass 155, 157 and 159 (3:4:1 in intensity; loss of Br from molecular ion), at mass 75 and 77 (3:1 in intensity; loss of HBr$_2$ from molecular ion), at mass 93 and 95 (1:1 in intensity; the CH$_2$Br+ ion), and at mass 49 and 51 (3:1 in intensity; the CH$_2$Cl+ ion).

The two other products had GC retention times of 9 and 11 minutes, respectively, and showed the mass spectra diagnostic for bromochloropropanols. The product having an 11 minute retention time was identified as 2-bromo-1-chloro-3-propanol: molecular mass ion at mass 172, 174 and 176 (3:4:1 in intensity) indicating the presence of one bromine atom and one chlorine atom on the molecule; major fragment mass ions at mass 136 and 138 (1:1 in intensity; loss of HCl from molecular ion), at mass 106 and 108 (1:1 in intensity; the CH$_2$CH-Br+ ion), and at mass 49 and 51 (3:1 in intensity; the CH$_2$Cl+ ion). The product having a 9 minute retention time was identified as 1-bromo-3-chloro-2-propanol: molecular mass ion at mass 172, 174 and 176 (3:4:1 in intensity) indicating the presence of one bromine atom and one chlorine atom on the molecule; major fragment mass ions at mass 123 and 125 (1:1 in intensity; loss of CH$_2$Cl from molecular ion), and at mass 79 and 81 (3:1 in intensity; loss of CH$_2$Br from molecular ion).

The following summarizes the products obtained:

| Product | % of Total Yield |
|---|---|
| Cl   Br   Cl<br>\|     \|     \|<br>CH$_2$ CH CH$_2$ | 22 |
| Cl   OH   Br<br>\|     \|     \|<br>CH$_2$ CH CH | 15 |
| Cl   Br   Br<br>\|     \|     \|<br>CH$_2$ CH CH | 63 |
| Total Yield = | 10.1 mg |

The seawater was diluted with a solution of KBr so that the following level of halide ion was present in the reaction solution:

| mM KBr | mM Cl$^-$ from Seawater |
|---|---|
| 40 | 400 |

Analysis of products by GC and GCMS was as outlined in Example 1, and the distribution and yield of products were essentially the same as for Reaction C of Example 1.

EXAMPLE 13

The procedure of Example 1 was followed, except potassium iodide was substituted for potassium chloride, and the following level of bromide ion and iodide ion was used:

| mM KI final | mM KBr final | mM Total Halide Ion |
|---|---|---|
| 20 | 3000 | 3020 |

Analysis of products by GC and GCMS was as outlined in Example 1. For the GC column temperature was set at 220° C., isothermal. Seven products were detected.

One product had a GC retention time of 23 minutes and showed the mass spectrum diagnostic for 2,3-diiodo-1-propanol: molecular mass ion not detected; major fragment mass ions at mass 254 (the I$_2$+ ion), at mass 185 (loss of I from molecular ion), at mass 127 (the I+ ion), and at mass 57 (loss of HI$_2$ from molecular ion).

Two other products had GC retention times 6 and 8 minutes, and showed the mass spectra diagnostic for iodo-propanediols. The product having a 6 minute retention time was identified as 1-iodo-2,3-propanediol: molecular mass ion at mass 202; major fragment mass ions at mass 171 (loss of CH$_2$OH from molecular ion) and at mass 75 (loss of I from molecular ion). The product having an 8 minute retention time was identified as 2-iodo-1,3-propanediol: molecular mass ion at mass 202; major fragment mass ions at mass 154 (loss of CH$_2$OH+OH from molecular ion) at mass 127 (the I+ ion) and at mass 75 (loss of I from molecular ion).

Another product had a GC retention time of 13 minutes, and showed the mass spectrum diagnostic for bromoiodo-1-propanol: molecular mass ion at mass 264 and 266 (1:1 in intensity) indicating one bromine atom on the molecule; major fragment mass ions at mass 206 and 208 (1:1 in intensity; the IBr+ ion), at mass 137 and 139 (1:1 in intensity; loss of I from the molecule), and at mass 127 (the I+ ion).

Another product had a GC retention time of 4 minutes and showed the mass spectrum diagnostic for 2,3-dibromo-1-propanol: molecular mass ion at mass 216, 218 and 220 (1:2:1 in intensity) indicating 2 bromine atoms on the molecule; major fragment mass ions at 137 and 139, and at 136 and 138 (both sets 1:1 in intensity; loss of Br and HBr, respectively, from molecular ion), and at 106 and 108 (1:1 in intensity; the $CH_2CHBr^+$ ion). This product had an identical GC retention time and mass spectrum with that of an authentic sample of 2,3-dibromo-1-propanol (purchased from Aldrich Chemical Company).

And two other products had GC retention times of 1 and 2 minutes, and showed the mass spectra diagnostic for bromopropanediols. The product having a 1 minute retention time was identified as 1-bromo-2,3-propanediol: molecular ion not detected; major fragment mass ions at mass 123 and 125 (1:1 in intensity; loss of $CH_2OH$ from molecular ion), and of mass 61 (loss of $CH_2Br$ from molecular ion). The product having a 2 minute retention time was identified as 2-bromo-1,3-propanediol: molecular mass ion not detected; major fragment mass ions at mass 136 and 138 (1:1 in intensity; loss of $H_2O$ from molecular ion), and at mass 106 and 108 (1:1 in intensity; the $CH_2CHBr^+$ ion).

Molecular iodine ($I_2$) was also formed.

The following summarizes the products obtained:

| Product | % of Total Yield |
| --- | --- |
| Bromoiodo-1-propanols | 42 |
| 2,3-Dibromo-1-propanol | 20 |
| Bromopropanediols | 8 |
| Iodopropanediols | 19 |
| 2,3-Diiodo-1-propanol | 11 |
| Total Yield = | 6.8 mg |

Further analysis of the bromoiodopropanol product was made using capillary gas chromatography-mass spectrometry ($GC^2$-MS) as described in Example 1.

2-Bromo-3-iodo-1-propanol had a $GC^2$ retention time of 8.8 minutes and showed the following diagnostic mass spectrum: molecular mass ion at mass 264 and 266 (1:1 in intensity) indicating one bromine atom on the molecule; major fragment mass ions at mass 233 and 235 (1:1 intensity; loss of $CH_2OH$ from molecular ion), at mass 206 and 208 (1:1 in intensity; the IBr+ ion), at mass 137 and 139 (1:1 in intensity; loss of I from molecular ion), at mass 127 (the I+ ion), at mass 106 and 108 (1:1 in intensity; the $CH_2CHBr^+$ ion), and at mass 57 (loss of HIBr from molecular ion).

3-Bromo-2-iodo-1-propanol had a $GC^2$ retention time of 8.6 minutes, and showed the following diagnostic mass spectrum: molecular mass ion at mass 264 and 266 (1:1 in intensity) indicating one bromine atom on the molecule; major fragment mass ions at mass 233 and 235 (1:1 in intensity; loss of $CH_2OH$ from molecular ion), at mass 206 and 208 (1:1 in intensity; the IBr+ ion), at mass 154 (the $CH_2CHI^+$ ion), at mass 137 and 139 (1:1 in intensity; loss of I from molecular ion), and at mass 57 (the loss of HIBr from molecular ion). The ratio of product formed was 1:1.3; 2-bromo-3-iodo-1-propanol: 3-bromo-2-iodo-1-propanol.

This procedure, like that of Example 5, also provides a method for the production of 2-bromo-3-iodo-1-propanol and 3-bromo-2-iodo-1-propanol, both of which are new compositions of matter.

As in Example 5, the bromoiodo-1-propanols were converted to epibromohydrin and epiiodohydrin by addition of lime or addition of Flavobacterium sp. whole cells to the reaction mixture.

Various modifications of the invention in addition to those exemplified and described herein will become apparent to those skilled in the art from the foregoing description. Such modifications are intended to fall within the scope of the appended claims.

REFERENCES CITED

U.S. Pat. Nos.

3,576,893; 4/1971; Baird Jr., et.al.
4,147,733; 4/1979; Fiske et.al.
4,247,641; 1/1981; Neidleman et.al.
4,426,449; 1/1984; Geigert and Neidleman.

Other Patents

Poland
   105,589; 1/1980; Dul e.al.
United Kingdom
   2,028,173A; (Application) filed 8/3/1979; Keller et.al.

Other Publications

1. Johnson, R. L. and D. W. Setser, *Journal of Physical Chemistry*, Vol. 71, 1967, pp. 4366–4383.
2. Roth, H. and H. R. Richardson, *Journal of Economic Entomology*, Vol. 63, 1970, pp. 496–499.
3. Rylander, P., *Catalytic Hydrogenation in Organic Synthesis*, Ch. 13, 1979, pp. 235–250.
4. Morrison, M. and G. R. Schonbaum, *Annual Reviews of Biochemistry*, Vol. 45, 1976, pp. 861–888.
5. Hager, L. P., D. R. Morris, F. S. Brown and H. Eberwein, *Journal of Biological Chemistry*, Vol. 241, 1966, pp. 1769–1777.
6. Bakkenist, A. R. J., J. E. G. DeBoer, J. Plat and R. Wever, *Biochimica et Biophysica Acta*, Vol. 613, 1980, pp. 337–348.
7. Morris, D. R. and L. P. Hager, *Journal of Biological Chemistry*, Vol. 241, 1966, pp. 1763–1768.
8. Cooney, C. L. and J. Hueter, *Biotechnology and Bioengineering*, Vol. 16, 1974, pp. 1045–1053.
9. Pickard, M. A., *Canadian Journal of Microbiology*, Vol. 27, 1981, pp. 1298–1305.

What is claimed is:

1. A method of making a vicinal dihalogenated product having adjacent bound carbons bound to different halogens from an alkene or alkyne which comprises (a) reacting the alkene or alkyne in an aqueous solution which includes (i) salts of at least two different halides; (ii) an oxidizing agent; and (iii) a halogenating enzyme selected from the group consisting of
   chloroperoxidase from *Caldariomyces fumago*;
   myeloperoxidase from leukocytes;
   lactoperoxidase from milk;
   bromoperoxidase from algae;
   thyroid peroxidase; and
   horseradish peroxidase;
provided that: if the enzyme is lactoperoxidase or bromoperoxidase, at least one of the halides is one with a standard oxidation potential higher than that of chloride; and, if the enzyme is thyroid peroxidase or horseradish peroxidase, at least one of the halides is one with a standard oxidation potential higher than that of bromide and (b) recovering a vicinial dihalogenated product having adjacent bound carbon bound to different halogens.

2. A method according to claim 1 wherein the oxidizing agent is hydrogen peroxide, the pH of the solution is between about 2.2 and about 8.0, there are two different halides in the solution, and the halide salts are selected from the group consisting of the fluoride, chloride, bromide and iodide of lithium, sodium and potassium.

3. A method according to claim 2 wherein the molar ratio of hydrogen peroxide to alkene or alkyne is between about 0.5:1 and about 50:1.

4. A method according to claim 3 wherein the ratio of the molar concentration of the halide ion which has the higher standard oxidation potential to the molar concentration of the other halide ion is between about 1:5 and about 1:500.

5. A method according to claim 4 wherein the alkene or alkyne is selected from the group consisting of ethylene, propylene, allyl chloride, allyl alcohol, 2-butene-1,4-diol and 2-butyne-1,4-diol.

6. A method according to claim 2 wherein the ratio of the molar concentration of the halide ion which has the higher standard oxidation potential to the molar concentration of the other halide ion is between about 1:5 and about 1:500.

7. A method according to claim 6 wherein the alkene or alkyne is selected from the group consisting of ethylene, propylene, allyl chloride, allyl alcohol, 2-butene-1,4-diol and 2-butyne-1,4-diol.

8. A method according to claim 1 wherein the oxidizing agent is hydrogen peroxide, the pH of the solution is between about 2.2 and about 8.0, at least two of the halides are selected from the group consisting of fluoride, chloride, bromide and iodide, and at least part of the amount of at least one of the halides selected from said group is provided by including in the solution seawater or other natural brine which contains at least one of the halides selected from said group.

9. A method according to claim 8 wherein the molar ratio of hydrogen peroxide to alkene or alkyne is between about 0.5:1 and about 50:1.

10. A method according to claim 9 wherein two halides, selected from the group consisting of fluoride, chloride, bromide and iodide, are present in the solution at a concentration greater than 1 mM and wherein the ratio of the molar concentration of the halide of said two halides which has the higher standard oxidation potential to the molar concentration of the other halide of said two halides is between about 1:5 and about 1:500.

11. A method according to claim 10 wherein the alkene or alkyne is selected from the group consisting of ethylene, propylene, allyl chloride, allyl alcohol, 2-butene-1,4-diol and 2-butyne-1,4-diol.

12. A method according to claim 8 wherein two halides, selected from the group consisting of fluoride, chloride, bromide and iodide, are present in the solution at a concentration greater than 1 mM and wherein the ratio of the molar concentration of the halide of said two halides which has the higher standard oxidation potential to the molar concentration of the other halide of said two halides is between about 1:5 and about 1:500.

13. A method according to claim 12 wherein the alkene or alkyne is selected from the group consisting of ethylene, propylene, allyl chloride, allyl alcohol, 2-butene-1,4-diol and 2-butyne-1,4-diol.

14. A method according to claim 1 wherein the hydrogen peroxide is generated in situ.

15. A method of making epifluorohydrin, epichlorohydrin, epibromohydrin or epiiodohydrin from allyl alcohol which comprises:
   (i) reacting the allyl alcohol in an aqueous solution at a pH between about 2.2 and 8, said solution including (a) salts of at least two different halides, one of which corresponds to the halogen in the epihalohydrin to be made; (b) hydrogen peroxide; and (c) a halogenating enzyme selected from the group consisting of:
   chloroperoxidase from *Caldariomyces fumago;*
   myeloperoxidse from leukocytes;
   lactoperoxidase from milk;
   bromoperoxidase from algae
   thyroid peoxidase; and
   horseradish peroxidase;
   provided that: if the enzyme is lactoperoxidase or bromoperoxidase, at least one of the halides is one which has a standard oxidation potential higher than that of chloride; and, if the enzyme is thyroid peroxidase or horseradish peroxidase, at least one of the halide ions is one which has a standard oxidation potential higher than that of bromide to form a vicinal dihalogenated product having adjacent bound carbons bound to different halogens;
   (ii) reacting the vicinal dihalogenated products from step (i) in aqueous solution either in the presence of an halohydrin epoxidase or by heating in the presence of strong base; and
   (iii) recovering epifluorohydrin, epichlorohydrin, epibromohydrin or epiiodohydrin.

16. A method according to any of claims 11-15 wherein the halogenating enzyme is chloroperoxidase from *C. fumago* and wherein the pH of the solution in which the halogenation reaction occurs is between about 2.5 and about 4.

17. A method according to any of claims 1-15 wherein the halogenating enzyme is chloroperoxidase from a culture of *C. fumago* (ATCC 16373) or *C. fumago* (NRRL 15272); and wherein the pH of the solution is which the halogenation reaction occurs is between about 2.5 and about 4.

18. A method according to any of claims 1-15 wherein the halogenating enzyme is lactoperoxidase from milk and wherein the pH of the solution in which the halogenation reaction occurs is between about 5 and about 7.5.

19. A method according to any of claims 1-15 wherein the halogenating enzyme is horseradish peroxidase and wherein the pH of the solution in which the halogenation reaction occurs is between about 5 and about 7.5.

* * * * *